(12) United States Patent
Biskup et al.

(10) Patent No.: US 9,365,503 B2
(45) Date of Patent: Jun. 14, 2016

(54) PROCESS FOR THE PREPARATION OF ISOCYANATES IN THE GAS PHASE

(75) Inventors: Klaus Biskup, Buchholz (DE); Rainer Bruns, Leverkusen (DE); Wolfgang Lorenz, Dormagen (DE); Lars Padeken, Itzehoe (DE); Bernd Pennemann, Gladbach (DE); Fritz Pohl, Brunsbuttel (DE); Andreas Rausch, Neuss (DE); Friedhelm Steffens, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 12/636,925

(22) Filed: Dec. 14, 2009

(65) Prior Publication Data

US 2010/0160674 A1 Jun. 24, 2010

(30) Foreign Application Priority Data

Dec. 19, 2008 (DE) .................. 10 2008 063 991

(51) Int. Cl.
*C07C 263/10* (2006.01)
(52) U.S. Cl.
CPC .................. *C07C 263/10* (2013.01)
(58) Field of Classification Search
None
See application file for complete search history.

(56) References Cited

U.S. PATENT DOCUMENTS

| 4,847,408 | A |  | 7/1989 | Frosch et al. |
| 5,081,303 | A | * | 1/1992 | Greenfield et al. ............ 564/419 |
| 5,391,683 | A |  | 2/1995 | Joulak et al. |
| 5,449,818 | A |  | 9/1995 | Biskup et al. |
| 5,728,880 | A |  | 3/1998 | Beckhaus et al. |
| 6,359,177 | B1 | * | 3/2002 | Brady et al. ............ 564/424 |
| 6,547,933 | B2 | * | 4/2003 | Marion et al. ............ 203/78 |
| 6,803,482 | B2 |  | 10/2004 | Jenne et al. |
| 6,930,199 | B2 |  | 8/2005 | Meyn et al. |
| 6,974,880 | B2 |  | 12/2005 | Biskup et al. |
| 7,307,190 | B2 |  | 12/2007 | Pennemann et al. |
| 7,342,134 | B2 |  | 3/2008 | Knoesche et al. |
| 7,541,487 | B2 |  | 6/2009 | Pohl et al. |
| 2005/0113601 | A1 |  | 5/2005 | Herold et al. |
| 2007/0015940 | A1 | * | 1/2007 | Pennemann et al. ........ 564/420 |
| 2007/0043233 | A1 |  | 2/2007 | Sanders et al. |
| 2010/0048942 | A1 | * | 2/2010 | Knoesche et al. ........... 560/347 |

FOREIGN PATENT DOCUMENTS

| CA | 2142911 | 3/1994 |
| WO | 02/43075 A1 | 6/2002 |
| WO | 2007028715 A1 | 3/2007 |
| WO | 2008071564 A1 | 6/2008 |
| WO | WO 2008071564 * | 6/2008 |

OTHER PUBLICATIONS

Willeboordse. Friso et al, Direct Gas Chromatographic Analysis of Isomeric Diaminotoluenes, Analytical Chemistry, Aug. 1968, vol. 40, No. 10, pp. 1455-1458.
Krauter, J.G.E. et al, Influence of Hydrogen Supply on By-Product Formation during the Hydrogenation of DNT to TDA, Science and Technology in Catalysis, 2002, pp. 427-430.

* cited by examiner

*Primary Examiner* — Sudhakar Katakam
*Assistant Examiner* — Jennifer C Sawyer
(74) *Attorney, Agent, or Firm* — Donald R. Palladino; Lyndanne M. Whalen

(57) ABSTRACT

Meta-toluene-diisocyanate is produced by reacting meta-toluenediamine with phosgene in the gas phase. The meta-toluenediamine to be vaporized for use in this phosgenation process must contain less than 0.5 wt. % of toluenediamine residue, a total of less than 0.2 wt. % of ammonia and cycloaliphatic amines, and less than 20 ppm of heavy metals. At least 0.1 wt. % of the liquid meta-toluenediamine being to be vaporized must not be vaporized. This non-vaporized content of the meta-toluenediamine must not be fed to the phosgenation reactor.

9 Claims, No Drawings

PROCESS FOR THE PREPARATION OF ISOCYANATES IN THE GAS PHASE

BACKGROUND OF THE INVENTION

The present invention relates to a process for the preparation of meta-toluene-diisocyanate by phosgenation of meta-toluenediamine in the gas phase.

Isocyanates are prepared in large amounts and serve chiefly as starting materials for the preparation of polyurethanes. They are usually prepared by reaction of the corresponding amine with phosgene. One possibility for the preparation of isocyanates is the reaction of the amine with the phosgene in the gas phase. In this process which is conventionally called gas phase phosgenation, the reaction conditions are chosen so that at least the reaction components amine, isocyanate and phosgene, but preferably all of the educts, products and reaction intermediate products, are gaseous under the conditions chosen. Among the advantages of gas phase phosgenation are, inter alia, a reduced phosgene hold-up, the avoidance of intermediate products which are difficult to phosgenate and increased reaction yields. The present invention relates exclusively to gas phase phosgenation.

Various processes for the preparation of diisocyanates by reaction of a diamine with phosgene in the gas phase are known from the prior art.

Specifically, phosgenation of aliphatic diamines in the gas phase has often been described. Thus, EP 289 840 B1 discloses a process for the preparation of diisocyanates by phosgenation of the corresponding diamine(s) in the gas phase, in which the vaporous diamine(s), optionally diluted with an inert gas or with the vapor of an inert solvent, and phosgene are heated separately to temperatures of from 200° C. to 600° C. and are reacted with one another continuously in a cylindrical reaction space while maintaining a turbulent flow. The gas mixture leaving the reaction space is passed through an inert solvent which is kept at a temperature above the decomposition temperature of the carbamic acid chloride corresponding to the diamine. The diisocyanate thereby dissolving in the inert solvent is subjected to working up by distillation.

The reaction of aromatic diamines with phosgene in the gas phase to give the corresponding diisocyanates is also described in the literature.

EP 593 334 B1 discloses a process for the preparation of aromatic diisocyanates in the gas phase in which a tube reactor is used. Mixing of the educts is achieved in this process by narrowing the walls of the tube reactor. The reaction is carried out in the temperature range of from 250 to 500° C. However, the process is problematic because the mixing of the educt streams solely by narrowing the tube wall functions poorly compared with the use of a proper mixing device. Poor mixing conventionally leads to an undesirably high formation of solids.

There have been many attempts to minimize this formation of solids which is particularly encountered in the reaction of aromatic diamines with phosgene in the gas phase, to make it possible to phosgenate aromatic diamines in the gas phase on a large industrial scale. In this context, the improvements in the process for the large-scale industrial phosgenation of aromatic amines in the gas phase focus on improving the mixing of the educt streams and equalizing the flow in the gas phase reactor, which lead to a prolonged service life of the gas phase reactor.

EP 570 799 B1 discloses a process for the preparation of aromatic diisocyanates, which is characterized in that the reaction of the associated diamine with the phosgene is carried out in a tube reactor above the boiling temperature of the diamine within an average residence time of from 0.5 to 5 seconds, and in which the average deviation from the average residence time is less than 6%. According to the teaching of EP 570 799 B1, both residence times which are too long and those which are too short lead to undesirable formation of solids, so that an equalizing of the flow in the reaction space is necessary, and above all back-mixing of the components in the reaction space is to be ruled out.

Measures for equalizing the flow conditions are likewise the subject matter of EP 1 362 847 B1. EP 1 362 847 B1 discloses a process for the preparation of aromatic diisocyanates in the gas phase in a tube reactor. In this process, control of the flow (e.g., equalizing and centering of the educt streams), and reduction in temperature variation with respect to time and an asymmetry in the temperature distribution make it possible, according to the teaching of EP 1 362 847 B1, to avoid caking and blockages in the reactor and therefore to a shortening of the service life of the reactors.

According to the teaching of EP 1 449 826 A1, the reaction of the aromatic diamine with phosgene in the gas phase the reaction of the phosgene with the diamine to give the diisocyanate competes with the secondary reaction of the diamine with the diisocyanate to give the corresponding urea oligomer. EP 1 449 826 A1 teaches that an improved mixing of the educts phosgene and diamine while simultaneously avoiding back-flow in the tube reactor increases the selectivity of the diisocyanate formation and reduces the formation of urea. As a result, according to the teaching of EP 1 449 826 A1, the amount of condensation product in the tubular reactor, which, because they are deposited on the reactor wall, lead to a reduction in the size of the free tube cross-section and to a gradual increase in pressure in the reactor and in the end determine the service life of the process, can be reduced. Apparatus solutions for improved mixing of the educts are likewise disclosed in EP 1 526 129 A1, DE 103 59 627 A1 and WO 2007/028 715 A; EP 1 526 129 A1 (flow measures for generating spin); DE 103 59 627 A1 (concentrically arranged annular nozzles with single); WO 2007/028 715 A (multiple amine feed); and EP 1 449 826 A1 (several amine nozzles arranged parallel to the axis of a tube reactor).

Nevertheless, not only the physical reaction conditions but likewise the properties of the aromatic diamines employed in the reaction with phosgene in the gas phase were the subject matter of the processes disclosed.

According to WO 2008/071 564 A, amines which are to be reacted in a gas phase phosgenation to give the corresponding isocyanates must meet certain requirements. Specifically, those amines which decompose to the extent of no more than 2 mol %, more preferably no more than 1 mol % and most preferably no more than 0.5 mol % under the reaction conditions prevailing in the gas phase reactor are suitable. According to the teaching of WO 2008/071 564 A, these are aliphatic or cyclic amines. According to WO 2008/071 564 A, aromatic amines can also be used if they can be converted into the gas phase without significant decomposition. WO 2008/071 564 A discloses that aromatic amines which are preferably suitable are toluenediamine (TDA), as the 2,4 or 2,6 isomer or as a mixture thereof, for example as an 80:20 to 65:35 (mol/mol) mixture; diaminobenzene; 2,6-xylidine; naphthyldiamine; and 2,4'- or 4,4'-methylene(diphenylamine) (MDA) and isomer mixtures thereof. However, instructions as to how the aromatic diamines which are described as preferably suitable can be converted into the gas phase without significant decomposition are not found in WO 2008/071 564 A.

EP 1 935 876 A1 also recommends the use of aromatic amines which can preferably be converted into the gas phase without decomposition. This specification discloses a process for the preparation of isocyanates in the gas phase, in which the reaction space has neither heating surfaces that can give rise to exposure to heat with the consequence of secondary reactions, such as isocyanurate or carbodiimide formation, nor cooling surfaces that can give rise to condensation and cause deposits.

EP 1 754 698 A1 discloses a specific vaporization technique which takes into account the exposure of the amine(s) employed in a gas phase phosgenation to heat. According to the teaching of EP 1 754 698 A1, the deposits observed in the reactor for reaction of the amine(s) with phosgene are caused by decomposition, during the reaction, of the amine(s) employed. This disclosure also teaches that long dwell times in the vaporization and superheating lead, specifically if aliphatic amine(s) are employed, to a partial decomposition of the amine(s) with ammonia being split off. This partial decomposition with splitting off of ammonia during the vaporization observed if aliphatic amities are employed not only reduces the yield, but results in the formation of deposits of ammonium chloride in the downstream pipelines and apparatus during the subsequent phosgenation reaction. The equipment must then be cleaned relatively frequently, resulting in production losses. EP 1 754 698 A1 states that these disadvantages occur in particular with the tube bundle heat exchangers, plate heat exchangers or falling film evaporators conventionally employed for the vaporization and superheating of the amines. As a technical solution, this disclosure teaches that the splitting off of ammonia during the vaporization is suppressed by employing specific milli- or micro-heat exchangers for the vaporization and superheating of the aliphatic amines. In the process disclosed, the amines are vaporized completely in the evaporator, so that circulation streams through the apparatus are eliminated, so that the amine flows through the apparatus only once.

The very small channels are a disadvantage of the micro heat exchangers disclosed in EP 1 754 698 A1. Very small amounts of solids, which are always present in industrial processes, already lead to a blockage and therefore reduce the service life of the evaporator. It is also a disadvantage that the amine to be vaporized should not contain any other not vaporizable constituents, because these other not vaporizable constituents would be deposited as a solid residue on the evaporator surface and therefore impair the heat transfer and finally lead to blocking of the evaporator. However, the provision of amines in the required quality is very involved and expensive in the industrial process. The service life of the reactor is improved by the teaching of the specification, but the service life of the evaporator system is impaired so significantly that the total service life of the production installation is not advantageously improved.

Minimizing exposure of the amines to heat during their vaporization for reaction with phosgene in the gas phase is likewise the subject matter of EP 1 935 876 A1. EP 1 935 876 A1 teaches that before the reaction with phosgene, the amines as a rule are vaporized and heated to 200° C. to 600° C. and are optionally fed to the reaction space in a form diluted with an inert gas (e.g., $N_2$, He or Ar), or with the vapors of an inert solvent (e.g., aromatic hydrocarbons, optionally with halogen substitution, such as chlorobenzene or o-dichlorobenzene). This disclosure teaches that the vaporization of the starting amine(s) can be carried out in any of the known vaporization apparatuses. Vaporization systems which are described as being preferred are those in which a small work content is led with a high circulating output over a falling film evaporator. Minimization of the exposure of the starting amine(s) to heat in the vaporization process is optionally assisted by feeding in inert gas and/or vapors of an inert solvent.

SUMMARY OF THE INVENTION

In spite of the attempts to optimize the reaction of aromatic amines with phosgene in the gas phase and thereby minimize the formation of solids, there is a further need to improve the gas phase phosgenation of aromatic diamines in order to make it possible to phosgenate aromatic diamines in the gas phase on a large industrial scale. It is an object of the present invention to provide a process for the gas phase phosgenation of aromatic diamines on a large industrial scale with minimal solids formation.

It has now been found, surprisingly, that the gas phase phosgenation of aromatic diamines on a large industrial scale depends on the quality of the aromatic diamines, and that control of the quality of the amines employed in combination with use of a specific vaporization technology substantially improves the service life of installations for the gas phase phosgenation of aromatic diamines.

DETAILED DESCRIPTION OF THE INVENTION

The improvement over prior art processes achieved by the process for the gas phase phosgenation of aromatic amines of the present invention requires an understanding of the composition of the raw materials employed.

It is known that aromatic amines can be prepared by catalytic hydrogenation of corresponding aromatic dinitro compounds. The hydrogenation can be carried out with solvents, such as methanol, ethanol or isopropanol or without such solvents. The hydrogenation can be carried out with the aid of catalysts dispersed in the reaction mixture. The catalyst may then be separated off by sedimentation or filtration and optionally fed back into the process, or retained in the reaction system by membrane filtration. Doped or non-doped Raney nickel catalysts and/or metal catalysts, which contain, for example, iridium, cobalt, copper, palladium or platinum, can be used as the catalyst. Such processes are known from the prior art. See, e.g., DE 2 135 154 B; DE 3 734 344 A1; EP 634 391 B1; DE 4 435 839 A1; EP 1 287 884 B1; EP 978 505 B1 and EP 1 033 361 B1.

In addition to the aromatic amine and the mandatory co-product water, organic by-products are also formed during the hydrogenation. The organic by-products are conventionally divided into the group of low-boiling substances and high-boiling substances based on their boiling point relative to the aromatic amine, or into various groups according to their chemical characteristics.

In the case of industrial nitration of toluene to give dinitrotoluene (DNT) and hydrogenation thereof to give toluenediamine (TDA), a TDA crude mixture which, in addition to water and toluenediamine, contains several such organic by-products is obtained as the product. The non-aqueous content of the crude TDA mixture is from 92 to 96 wt. % of the m-TDA isomers (2,4- and 2,6-TDA), less than 1 wt. % of the para-TDA isomer (2,5-TDA), 3 to 5 wt. % of low-boiling substances and 0.2 to 2 wt. % of high-boiling substances, the percentages in each case adding up to 100 wt. %.

m-TDA isomers in the context of the present invention denotes an isomer mixture of 2,4-TDA and 2,6-TDA. An isomer mixture of from 78 to 82 wt. % of 2,4-TDA and 18 to 22 wt. % of 2,6-TDA is preferably achieved. However, m-TDA isomer mixtures with isomer ratios which deviate from these ranges and also the separate use of technically pure 2,4- or 2,6-TDA isomers are also suitable for use in the process of the present invention for the reaction of aromatic diamines with phosgene in the gas phase. This is taken into account by the use of the term meta-toluenediamine at a suitable point.

In the context of the present invention, low-boiling substances are compounds which have a lower boiling point than the two m-TDA isomers, and high-boiling substances are those compounds which have a higher boiling point than the two m-TDA isomers.

The non-aqueous content of the crude TDA mixture generally includes, in addition to the TDA isomers, toluidines and ammonia, each of which are low-boiling substances, and cycloaliphatic amines. In the context of this invention, the group of cycloaliphatic amines includes compounds which have been formed from one of the TDA isomers or from toluidine by hydrogenation of the aromatic ring and may optionally contain oxygen-containing groups, such as keto or hydroxyl groups. Cycloaliphatic amines can be low- or high-boiling substances.

The composition of TDA isomer mixtures and their content of low-boiling substances and cycloaliphatic amines are conventionally determined using gas chromatography methods which are known to the person skilled in the art. For example, the method of Willeboordse et al. (Willeboordse, F.; Quick, Q.; Bishop, E. T. "Direct gas chromatographic analysis of isomeric diaminotoluenes" Analytical Chemistry 1968, 40 (10), 1455-1458) is suitable.

Colored oligomeric species are often formed by oxidative coupling of two TDA isomers. These species are to be assigned to the group of high-boiling substances and are in general called the TDA residue (Krauter, J. G. E.; Groβ, M.; Panster, P.: "Influence of Hydrogen Supply on By-Product Formation during the Hydrogenation of DNT to TDA", Science and Technology in Catalysis 2002, 427-430). WO 2005/066113 A1 describes the TDA residue as oligomers and polymers essentially composed of azo, azoxy or hydrazine compounds. In addition, this specification indicates that the TDA residue can also contain residues of the catalyst, that is to say heavy metals, such as iridium, copper, cobalt, nickel, iron, palladium or platinum. EP 659 173 B1 describes as possible constituents of the TDA residue diphenylmethanes, diphenylamines, acridines and phenazines, i.e., compounds which contain at least two aromatic rings.

In the context of the present invention, the term TDA residue likewise describes collectively organic compounds which contain at least two aromatic rings but can carry the most diverse functional groups. In the context of the present invention, it is furthermore to be understood that the TDA residue can be a mixture of the organic compounds mentioned with residues of the catalyst, i.e., heavy metals, such as iridium, copper, cobalt, nickel, iron, palladium and/or platinum.

The content of TDA residue is conventionally determined by residue distillation, the weight content of the TDA residue in a sample being determined by weighing before and after TDA isomers, cycloaliphatic amines and optionally further low-boiling substances have been distilled off. The content of heavy metals, i.e., all metals which have a higher atomic number than the element titanium in the Periodic Table of the Elements, can be determined by methods known to the person skilled in the art, e.g., by means of atomic adsorption spectroscopy.

The crude TDA mixture obtained in the hydrogenation is conventionally purified for further use. The purification can be carried out by distillation, crystallization and/or after-treatment with heat as well as chemical oxidation or reduction processes.

In large-scale industrial processes, the purification process is preferably carried out by distillation, and in this way the water of reaction and low-boiling substances, such as ammonia, hexahydro-toluidine, hexahydro-toluenediamine and optionally solvents, are partly or completely removed. This separation of water, low-boiling substances and optionally also solvents can be carried out in one or more stages. Preferably, removal of one or more of the ortho-toluenediamine isomers by distillation is carried out thereafter, it being possible for this separation of o-TDA by distillation to be carried out in one or more stages. The content of o-TDA is thereby preferably reduced to less than 0.3 wt. % (Kirk-Othmer Encyclopedia of Chemical Technology, A. R. Cartolano: Toluenediamine, John Wiley & Sons, 2001).

After the distillation steps for working up the crude TDA mixture, a further concentration of the m-TDA can be carried out by separation of the TDA residue from the remaining m-TDA. According to the prior art, the TDA residue is conventionally separated from the m-TDA by distillation. There have been a number of attempts to separate the TDA residue continuously and with the lowest possible energy input and loss of m-TDA. All of these attempts lead to an m-TDA which can be called free from TDA residue in the technical sense, but this m-TDA which is pure in the technical sense is never completely free from residue because a certain amount of residue is formed again during exposure to heat.

EP 659 173 B1 mentions the separation of TDA residue from m-TDA as advantageous, because the formation of higher molecular weight compounds in the reaction of the amine with phosgene to give the diisocyanate in the liquid phase is thereby reduced and the necessary discharge of these higher molecular weight components from the TDI process is reduced. (Ullmann, 4th edition, volume 13, p. 351). EP 659 173 B1 also teaches that only residue-free m-TDA can be employed in the gas phase phosgenation. Nevertheless, this assertion that exclusively residue-free TDA can be used for the gas phase phosgenation is not stated in more detail in the specification of EP 659 173 B1.

Overall, EP 659 173 B1 discloses a process for separating the residue, in which the m-TDA can be separated from the TDA residue with the aid of auxiliary substances foreign to the TDA mixtures and having a boiling point above 290° C. A residue/auxiliary substance mixture having an m-TDA content of 1-5 wt. % is obtained.

EP 794 170 B1 describes the process disclosed in EP 659 173 B1 as disadvantageous, since the ratio of residue to auxiliary substances is at best only 1:2. In addition to the costs for the auxiliary substances and disposal thereof, the high expenditure of energy to achieve the required bottom temperature of 290° C. necessary for separating the m-TDA completely must be taken into account. EP 794 170 B1 discloses, instead of an auxiliary substance foreign to the TDA mixture, use of o-TDA as an entraining agent. A residue-containing stream containing 50 wt. % of residue, 40 wt. % of o-TDA and 10 wt. % of m-TDA isomers, which is put to heating use, can thereby be obtained. The m-TDA content of 10 wt. % remaining in the residue-containing stream represents a significant economic loss.

The preparation of an m-TDA which is pure in the technical sense by separating the residue from m-TDA using o-TDA as an entraining agent is likewise the subject matter of WO 2002/048075 A1. In the process disclosed in WO 2002/048075 A1, the m-TDA in the residue-containing stream is replaced by o-TDA using a stripping column, and not by simple mixing and distillation as in EP 794 170 B1. The m-TDA content in the residue-containing stream can thereby be lowered to below 0.9 wt. %, in some cases to values below the detection limit.

In return, an m-TDA which essentially contains the 2,4- and 2,6-TDA isomers and contains only approx. 0.1 wt. % (1,000 ppm) of o-TDA and only approx. 0.1 wt. % of TDA residue is obtained. The disadvantage of this process is the increased expenditure on apparatus and energy which is required.

EP 1 746 083 A1 solves the requirement of an increased expenditure on apparatus by separating the crude TDA into at least four product streams P1-P4 by distillation in a dividing wall column. The product stream P1 is a stream containing low-boiling substances. The product stream P2 is a stream containing o-TDA and the product stream P3 is a stream containing m-TDA. The product stream P4 is a product stream containing high-boiling substances and m-TDA. By this process, for example, a product stream P3 which, in addition to m-TDA, also contains 0.59 wt. % of p-TDA and only 0.1 wt. % of o-TDA and is residue-free in the technical sense can be obtained. m-TDA can be separated from the product stream P4 of the dividing wall column in an additional apparatus. This can be carried out by distillation methods in the context of the abovementioned prior art, or, for example, by the use of a kneader dryer, which is operated under heat in vacuo.

Processes for converting a crude TDA such as that obtained from the hydrogenation of DNT on a large industrial scale into an m-TDA which is free from residue in the technical sense are known to those skilled in the art. The prior art (EP 659 173 B1) furthermore recommends that only residue-free m-TDA should be employed in the reaction with gaseous phosgene.

In view of the teachings in the prior art, those skilled in the art expect that the technically pure m-TDA obtained after separating the residue can be vaporized by known methods and therefore be fed completely to the gas phase phosgenation.

It has been surprisingly found, however, that this procedure which emerges from the prior art and is extremely advantageous with respect to the flow of substances has not proven itself. To the contrary, it has proven to be unusable for carrying out the gas phase phosgenation of m-TDA in an economical manner.

The complete conversion of a technically pure m-TDA into the gas phase for the purpose of phosgenation in the gas phase surprisingly does not lead to the purity of the vaporous TDA required for the gas phase phosgenation, but to formation of large amounts of ammonia. This release of ammonia during complete vaporization of m-TDA leads to deposits of ammonium chloride both in the subsequent phosgenation reaction and in the downstream pipelines and apparatus. These installations must then be cleaned relatively frequently causing corresponding production losses. It has furthermore been found that an m-TDA which has been freed from its residue according to the prior art and can be called free from TDA residue in the technical sense is never completely residue-free, because certain amounts of residue are formed again during exposure to heat. Specifically, in the complete conversion of the m-TDA into the gas phase as recommended in the prior art, this residue leads to deposits in the evaporator systems and therefore to a limited service life of the evaporator systems or the installations for phosgenation of m-TDA in the gas phase.

The object of the present invention was therefore to provide a simple process for the preparation of m-TDA by phosgenation of m-TDA in the gas phase with an m-TDA vaporization, which is distinguished by a low release of ammonia with a simultaneously high service life of the vaporization apparatus, and therefore ensures a reduced occurrence of troublesome solids and the associated caking, blockages and downtimes and is therefore distinguished by a considerably increased number of operating hours.

It has been possible to achieve this objective by keeping the content of materials which promote the release of ammonia as low as possible in the m-TDA to be vaporized for the purpose of phosgenation in the gas phase. The m-TDA to be vaporized for the purpose of phosgenation in the gas phase should of course also contain as little physically dissolved ammonia as possible.

The nature and content of the impurities contained in the m-TDA to be vaporized considerably influence the degree of release of ammonia during the vaporization. When the m-TDA vaporizes, the concentration of the impurities increases and the extent of the release of ammonia increases further. Undesirable isomers of m-TDA are not impurities in this context. Impurities which promote an increased release of ammonia are TDA residue, cycloaliphatic amines and heavy metals. Heavy metals, in particular nickel, greatly contribute to a high release of ammonia (Example 1) and accumulate in the bottom of the evaporator during the vaporization of m-TDA.

It has been found, surprisingly, that separating off from the m-TDA the impurities which promote the release of ammonia is not by itself an adequate measure for fulfilling the object of the present invention because amounts of ammonia which are still sufficient to cause significant deposits in the process of gas phase phosgenation can form from technically pure m-TDA during corresponding exposure of the technically pure m-TDA to heat. This observation is explained by the fact that certain amounts of residue are formed again during exposure to heat (Example 2).

It has been possible, surprisingly, to achieve the reduction in the release of ammonia to an industrially advantageous extent and to increase considerably the number of operating hours of the gas phase phosgenation of m-TDA while simultaneously improving the service life of the vaporization systems employed by a combination of measures, which combination cannot be deduced from the prior art.

The first measure is use of an m-TDA which contains the lowest possible contents of ammonia, TDA residue, cycloaliphatic amines and heavy metals in the vaporization. This measure in combination with the second and third measures minimizes the formation of impurities and ammonia from the technically pure m-TDA during heating for the purpose of vaporization. A second measure is conduct of the vaporization of the m-TDA under conditions such that the ratio between the amount of liquid V [kg] present in the evaporator and the gas stream $\dot{M}$ [kg/h] leaving the evaporator is less than 2 h.

$$\frac{V}{\dot{M}} < 2h$$

where
V=amount of liquid in the m-TDA evaporator [unit: mass]; the amount of liquid V includes the amount of liquid present in the evaporator in [kg], which for example in the case of pumped circulation or circulatory evaporators also includes the amount of liquid in the pumped circulation or in the circulation; and
$\dot{M}$=the gas stream $\dot{M}$ leaving the evaporator [unit: mass/time].

A third measure useful in the process of the present invention is that the m-TDA fed to the evaporator is not vaporized completely, but a content of at least 0.1 wt. % is always sluiced out of the evaporator, and this remaining content is not introduced into the reactor for reaction of the m-TDA with phosgene.

The present invention therefore provides a process for the preparation of meta-toluene-diisocyanate by reaction of meta-toluenediamine with phosgene in the gas phase, in which the meta-toluenediamine and the phosgene are fed separately in gaseous form to a reactor.

The gaseous meta-toluenediamine used in the phosgenation process of the present invention is generated by vaporization in at least one evaporator. The liquid meta-toluenediamine fed to the evaporator contains less than 0.5 wt. %, preferably between 0.01 wt. % and 0.1 wt. %, based on the weight of meta-toluenediamine, of toluenediamine residue, and in total less than 0.2 wt. %, based on the weight of meta-toluenediamine, of ammonia and cycloaliphatic amines. The liquid meta-toluenediamine fed to the evaporator contains less than 20 ppm, preferably between 0.05 ppm and 10 ppm, based on the weight of meta-toluenediamine, of heavy metals. The ratio between the amount of liquid V [kg] present in the evaporator and the gas stream M [kg/h] leaving the evaporator is preferably less than 2 h. The meta-toluenediamine fed to the evaporator is partly vaporized, a content of the meta-toluenediamine of at least 0.1 wt. %, based on the weight of meta-toluenediamine, not being vaporized. The non-vaporized content of the meta-toluenediamine is not fed to the reactor.

In a particularly preferred embodiment of the present invention, the meta-toluenediamine fed to the vaporizer contains a1) less than 50 ppm, preferably between 0.1 and 20 ppm, based on the weight of meta-toluenediamine, of ammonia and a2) less than 0.1 wt. %, preferably between 0.01 and 0.05 wt. %, based on the weight of meta-toluenediamine, of cycloaliphatic amines.

Data in ppm relate to the weight, i.e. 1,000 ppm correspond to 0.1 wt. %. The limit values stated for the content of heavy metals, ammonia, cycloaliphatic amines and TDA residue in the m-TDA fed to the evaporator apply at the point in time of entry of the m-TDA into the evaporator. In practice, any samples taken should be prepared for analysis as rapidly as possible, i.e. as far as possible within 60 min.

In a preferred embodiment of the present invention, the toluenediamines employed are obtained by catalytic hydrogenation of corresponding dinitrotoluenes. The hydrogenation can be carried out with the use of solvents, such as methanol, ethanol or isopropanol, but also without such solvents. The hydrogenation can be carried out with the aid of catalysts dispersed in the reaction mixture, which are then separated off by sedimentation or filtration and optionally fed back into the process. Doped or non-doped Raney nickel catalysts or metal catalysts, which contain, for example, iridium, cobalt, copper, palladium or platinum, can be used as the catalyst. In the industrial hydrogenation of dinitrotoluene (DNT) to give toluenediamine (TDA), a crude TDA mixture is obtained as the product, which in addition to water contains several organic compounds which are essentially composed of 92 to 96 wt. % of the m-TDA isomers (2,4- and 2,6-TDA), of less than 1 wt. % of the p-TDA isomer (2,5-TDA), 3 to 5 wt. % of low-boiling substances and 0.2 to 2 wt. % of high-boiling substances, the percentages in each case adding up to 100 wt. %. The group of high-boiling substances also contains oligomeric, often colored species which are formed by oxidative coupling of two TDA isomers and are in general called TDA residue. A definition of the term residue in the context of the invention is given above.

The crude TDA mixture obtained in the hydrogenation is purified for further use. The purification process is preferably carried out by distillation, with the water of reaction and low-boiling substances, such as ammonia, hexahydro-toluidine, hexahydro-toluenediamine and optionally solvents, being partly or completely removed. This separation of water, low-boiling substances and, optionally, also solvents can be carried out in one or more stages. Preferably, removal of one or more of the o-TDA isomers by distillation is carried out thereafter. This separation of o-TDA by distillation may be carried out in one or more stages. Preferably, after this distillation, a further concentration of the m-TDA is carried out by separating the high-boiling substances from the m-TDA which remains and obtaining in this way an m-TDA product stream which is residue-free in the technical sense.

In a preferred embodiment, after the substantial removal of water, low-boiling substances and, optionally, solvents described above, the m-TDA is processed to give an m-TDA which is technically pure in the context of the present invention by separating low-boiling substances and high-boiling substances in a dividing wall column. A technically pure m-TDA in the context of the present invention is any m-TDA which contains less than 0.5 wt. %, based on weight of m-TDA, of toluene diamine residue, and in total less than 0.2 wt. %, based on weight of m-TDA, of ammonia and cycloaliphatic amines and contains less than 20 ppm of heavy metals. The purification is most preferably carried out in a dividing wall column in which a dividing wall is arranged in the longitudinal direction of the column to form an upper common column region, a lower common column region which is optionally present, a feed part with a rectification part and stripping part, and a removal part with a rectification part and stripping part. This purification process preferably includes the following steps:

A) feeding of the educt steam into the feed part of the dividing wall column,

B) stripping off of a low-boiling substance fraction over the column head,

C) stripping off of TDA over a lateral take-off in the removal part of the dividing wall column, and D) stripping off of a high-boiling substance fraction via the bottom of the column.

The feed to the dividing wall column essentially (i.e., preferably at least 75 wt. %, more preferably at least 87 wt. %, most preferably at least 93 wt. %) contains m-TDA and preferably additionally contains less than 10 wt. % of o-TDA, less than 5 wt. % of high-boiling substances, less than 5 wt. % of low-boiling substances and less than 5 wt. % of water. The data reported in wt. % here in each case relate to the weight of the feed to the dividing wall column. Preferably, the separation is carried out under an absolute overhead pressure of between 50 and 2,000 mbar, more preferably between 60 and 500 mbar and most preferably between 70 and 200 mbar. The column preferably has at least 5 theoretical separating stages in the stripping part of the removal section. For the efficiency of the stripping part of the removal section, some of the liquid flowing out of the rectifying part must be introduced into the stripping part. The amount is chosen so that the content of high-boiling substances in the m-TDA taken off from the removal part is less than 0.1 wt. %, based on the weight of the m-TDA taken off.

In this context, any of the installed units known to those skilled in the art, such as perforated, bubble or valve trays or ordered or non-ordered packing, can be employed as a separating aid. The pressure loss due to the separating aid should be kept low. The pressure loss is preferably less than 150 mbar and most preferably less than 100 mbar. Heaps of packing and ordered packing preferably have a specific surface area of from 100 to 500, most preferably from 200 to 350 m²/m³. The bottom temperature is determined by the contents of high-boiling substances and the pressure loss in the column; the operating conditions of the column are preferably chosen so that bottom temperatures of less than 260° C., preferably less than 240° C., result.

In another preferred embodiment of the present invention, m-TDA which is technically pure in the context of the present invention is prepared by purification of the m-TDA in an arrangement of columns in which a common overhead column is connected to a feed column, a removal column and optionally a common bottom column. In this context, vapors from the feed and removal column are passed into the overhead column, while the liquid draining out of the overhead columns is distributed between the feed and removal column. The vapor of the bottom column, optionally present, is passed into the feed and removal column, while the liquids draining out of the feed and removal column are passed to the bottom column, optionally present.

In a further preferred embodiment of the present invention, an m-TDA which is technically pure in the context of the present invention is prepared by purification of the m-TDA in an arrangement of columns in which the crude TDA is first freed from low-boiling substances and o-TDA and the bottom product obtained in this way are freed from high-boiling substances in an additional column. The column preferably has at least 5 theoretical separating stages in the rectifier part. The reflux to the column should be chosen so that the content of high-boiling substances in the top product is less than 0.1 wt. %, based on the weight of the top product. Even if gentle vaporization conditions are chosen, formation of residue may occur in the evaporator or in the column, as a result of which ammonia is released. Because the m-TDA is obtained as the top product in this embodiment of the present invention, the conditions under which the condensation is carried out should be chosen so that a product with preferably less than 50 ppm of dissolved ammonia is obtained. This is made possible by a sufficiently high condensation temperature, at which only little ammonia is dissolved in the condensation product. Alternatively or additionally, for example, an inert gas may be introduced into this distillation step. This inert gas acts as an entraining agent for ammonia and effects transportation of the ammonia away via the devolatilization path of the column.

Purification of the crude TDA mixture should be carried out under conditions such that the m-TDA obtained is pure in the technical sense (i.e., contains in total less than 0.5 wt. % of TDA residue, preferably less than 0.1 wt. % of TDA residue, and in total less than 0.2 wt. % of impurities, preferably less than 0.1 wt. % of cycloaliphatic amines, less than 50 ppm of ammonia and less than 10 ppm of heavy metals, in each case based on the weight of m-TDA). The storage of the m-TDA is likewise to be taken into account when carrying out the process of the present invention. TDA residue can form during storage of the m-TDA which is pure in the technical sense or by contact with air. The m-TDA which is pure in the technical sense therefore conventionally contains small amounts of TDA residue, i.e., the content of TDA residue is conventionally greater than 0 wt. % and preferably less than 0.1 wt. %.

When used for the gas phase phosgenation, the meta-toluenediamine obtained by any one of the above-mentioned preferred embodiments is vaporized in at least one evaporator and heated to a temperature of from 200° C. to 600° C., preferably from 200° C. to 500° C., most preferably from 250° C. to 450° C., and optionally fed to the reaction space in a form diluted with an inert gas, such as $N_2$, He or Ar, or with the vapors of an inert solvent, e.g. aromatic hydrocarbons, optionally with halogen substitution such as chlorobenzene or ortho-dichlorobenzene.

In the process of the present invention, the stream fed to the evaporator which has been obtained by one of the above-mentioned preferred embodiments is partly vaporized, i.e. preferably to the extent of at least 70 wt. %, more preferably to the extent of at least 90 wt. %, most preferably to the extent of at least 95 wt. %, based on the weight of the m-TDA, but is not vaporized to the extent of at least 0.1 wt. %, preferably to the extent of at least 0.5 wt. %, most preferably to the extent of at least 1.0 wt. %, based on the weight of the m-TDA. The high-boiling substances introduced with the m-TDA and the impurities formed by heating the m-TDA, which promote the release of ammonia, accumulate in this non-vaporized portion. The non-vaporized portion is sluiced out of the evaporator continuously or batchwise and is not fed to the gas phase reactor. Preferably, the non-vaporized portion is fed partly or completely again to the working up of the crude TDA by distillation described above. In a further embodiment which is likewise preferred, the non-vaporized portion can be discharged from the evaporator continuously or batchwise and disposed of, preferably disposed of by means of heat. In another embodiment which is likewise preferred, the non-vaporized portion can be discharged from the evaporator continuously or batchwise and partly, preferably to the extent of 10 to 90%, fed directly into the evaporator again with the technically pure m-TDA.

Any evaporator can in principle be employed as an evaporator for the amine vaporization. Tube bundle heat exchangers, plate heat exchangers or falling film evaporators, optionally with pumped circulation, can preferably be employed. Micro-heat exchangers or micro-evaporators such as those described in WO 2005/016512 A or in DE 10 2005 036870 A1 can also be employed if they are used only for partial vaporization of the m-TDA stream fed to the evaporator.

In a preferred embodiment, the vaporization of the meta-toluenediamine is carried out in a falling film evaporator with pumped circulation. The m-TDA vaporized in the falling film evaporator at temperatures above its boiling point is fed to the reactor for the purpose of gas phase phosgenation, while the non-vaporized content of the evaporator feed stream is not fed to the reactor. The non-vaporized content of the evaporator feed stream is separated from the vaporized m-TDA, it being possible for the separation to be carried out in one or more stages and by simple condensation, by varying the flow ratios or optionally with the use of droplet separators. The non-vaporized content of the evaporator feed stream is collected in the pump reservoir of the falling film evaporator and can be partly fed back from there to the falling film evaporator and/or completely or partly introduced back into the TDA distillation sequence and/or completely or partly sluiced out and removed for disposal. If the non-vaporized content is partly fed back to the falling film evaporator and/or completely or partly introduced back into the TDA distillation sequence, this is preferably carried out continuously. If the non-vaporized content is partly fed back to the falling film evaporator and/or completely or partly sluiced out and removed for disposal, this can be carried out continuously or discontinuously, preferably discontinuously. A reduction in the amount of liquid V in the m-TDA evaporator has an advantageous effect on the suppression of the formation of ammonia and other impurities. When a falling film evaporator with a pumped circulation and pump reservoir is used, the amount of liquid V includes the amount of liquid in the falling film evaporator, in the pumped circulation and in the pump reservoir. In all of these embodiments, the ratio between the amount of liquid V kept in the bottom of the evaporator corresponding to the definition given above and the stream Ṁ converted into the gas phase in the evaporator is adjusted so that it is less than 2 h. This ensures that the stream of meta-toluenediamine which is technically pure in the context of this invention and is fed to the evaporator releases sufficiently little ammonia within the evaporator.

The vaporization and superheating of the m-TDA is preferably carried out in several stages in order to avoid non-vaporized droplets in the vaporous TDA stream. Multi-stage vaporization and superheating steps in which droplet separators are incorporated between the vaporization and superheating systems and/or the vaporization apparatus also have the function of a droplet separator are particularly preferred. Suitable droplet separators are described, e.g., in "Droplet Separation", A. Bürkholz, VCH Verlagsgesellschaft, Weinheim—New York—Basel—Cambridge, 1989. Droplet separators which cause a low pressure loss are particularly preferred. Most preferably, the vaporized amine is brought to the desired use temperature via at least one after-heater, which also functions as a droplet separator. It is preferred that this after-heater have a liquid drain in order to ensure constant emptying of the separator.

After leaving the last superheater in the direction of flow, the vaporous amine which has been preheated to its intended temperature is fed with an average dwell time of from preferably 0.01 to 60 s, more preferably from 0.01 to 30 s, most preferably from 0.01 to 15 s, to the reactor or the mixing device thereof for reaction. The risk of renewed formation of droplets is counteracted via technical measures, e.g., adequate insulation to avoid losses by radiation. The reactor running time is increased significantly by generation of an essentially droplet-free vaporous flow of starting amine before entry into the reactor. An essentially droplet-free vaporous stream of starting amine means that the vaporous amine contains essentially no droplets of non-vaporized amines, that is to say that a maximum of 0.5 wt. % of the amine, most preferably a maximum of 0.05 wt. % of the amine, based on the total weight of amine, is present in the form of non-vaporized droplets and the remaining portion of the amine is present in vaporous form. Most preferably, the vaporous amines contain no droplets of non-vaporized amines. In the context of the present invention, the droplets of non-vaporized amine optionally present in the otherwise vaporous stream of amine are not to be counted as part of the at least 0.1 wt. % of m-TDA which is not vaporized and not fed to the reactor. Regardless of any entrained amine droplets in the vaporous stream of amine, a content of at least 0.1 wt. % of meta-toluenediamine, based on the weight of meta-toluenediamine, is not vaporized in the process of the present invention and is not fed to the reactor in which the phosgenation is conducted.

The amounts of liquid separated out are optionally brought together with the non-vaporized TDA from the evaporator.

The evaporator and/or superheater and the pipelines for generation of the vaporous stream of m-TDA to the gas phase reactor can be produced from any desired metallic material, e.g., steel, high-grade steel, titanium, Hastelloy, Inconel or other metallic alloys. Metallic materials with a low nickel content are preferably used.

The stream of vaporized m-TDA, optionally diluted with an inert gas or with the vapor of an inert solvent, is heated to a temperature of from 200° C. to 600° C. and is reacted continuously with a stream of phosgene, optionally diluted with an inert gas or with the vapors of an inert solvent, which has been heated separately from the stream of amine to a temperature of from 200° C. to 600° C. in a tube reactor with a constant or changing cross-section, while maintaining a turbulent flow, within an average dwell time of from 0.5 to 15 seconds. The gas mixture leaving the reaction space is passed through at least one inert solvent and/or through at least one mixture of inert solvent and diisocyanate, the solvent or the mixture being kept at a temperature above the decomposition temperature of the carbamic acid chloride corresponding to the diamine. The diisocyanate dissolved in the inert solvent is subjected to working up by distillation.

In a further preferred variant of the invention, the non-vaporized stream of the m-TDA is completely or partly sluiced out and removed for disposal or completely or partly sluiced out and introduced into the TDA distillation sequence. After sluicing out and before disposal or feeding into the TDA distillation sequence, it is preferred that this non-vaporized stream be cooled to a temperature below the boiling temperature of the TDA in the evaporator, preferably to a temperature below 260° C., most preferably to a temperature below 200° C. In this procedure, however, the temperature should not fall below 100° C., most preferably not below 130° C. The cooling can take place in any of the known heat exchangers, such as tube bundle heat exchangers or plate heat exchangers. Water, condensate, secondary coolant circulations, air and/or other streams which are to be heated can be used as the coolant. Cooling preferably takes place by means of streams of materials which are to be heated, most preferably a stream of TDA.

In a further embodiment of the process of the present invention, an m-TDA which is distinguished by a low release of ammonia during the vaporization is obtained by heat treatment at high temperatures for a relatively long dwell time of an m-TDA which has been freed from low-boiling substances and o-TDA but can still contain high-boiling substances. The temperatures used for this heat treatment are preferably 100 to 350° C., more preferably 130 to 330° C. and most preferably 200 to 320° C., while the dwell time at this temperature is longer than 15 minutes, more preferably from 20 minutes to 10 days, most preferably from 30 minutes to 4 hours. This heat treatment is advantageous because the reactions which lead to the formation of ammonia proceed to a noticeable extent and the ammonia thereby formed can be separated off. The m-TDA obtained after the ammonia has been separated off will have a lower tendency to split off ammonia during the subsequent vaporization.

The present invention also relates to a process for the preparation of meta-toluene-diisocyanate by reaction of meta-toluenediamine with phosgene in the gas phase, in which the meta-toluenediamine and the phosgene are fed separately from one another in gaseous form to a reactor. The gaseous meta-toluenediamine is generated by vaporization in at least one evaporator of a liquid meta-toluenediamine which
a) contains in total less than 0.2 wt. %, based on the weight of meta-toluenediamine, of ammonia and cycloaliphatic amines, and
b) contains less than 20 ppm of heavy metals, and
c) has been heat treated at not less than 100° C. for at least 15 minutes so that the ammonia thereby formed is removed.

This embodiment of the process of the present invention also requires that the meta-toluenediamine fed to the evaporator have the purity specified above with respect to ammonia, cycloaliphatic amines and heavy metals. However, the purity of the m-TDA alone is not sufficient and must therefore be combined with at least one further measure. In this embodiment of the invention, this further measure is the heat treatment of the meta-toluenediamine before the vaporization. During the heat treatment, a residue content of more than 0.5 wt. % can be tolerated. After this heat treatment, an exact adjustment of the ratio between the amount of liquid V [kg] present in the evaporator and the gas stream M [kg/h] leaving the evaporator to a value of less than 2 h is no longer absolutely necessary.

EXAMPLES

The composition of TDA isomer mixtures and their content of cycloaliphatic amines are conventionally determined using gas chromatography methods known to those skilled in the art. The method of Willeboordse et al. is suitable (Willeboordse, F.; Quick, Q.; Bishop, E. T. "Direct gas chromatographic analysis of isomeric diaminotoluenes" Analytical Chemistry 1968, 40 (10), 1455-1458).

The content of TDA residue is conventionally determined by residue distillation, the weight content of the TDA residue in a sample being determined by weighing before and after TDA isomers, cycloaliphatic amines and optionally further low-boiling substances have been distilled off.

The content of heavy metals can be determined by methods known to the person skilled in the art by means of atomic adsorption spectroscopy.

The content of physically dissolved ammonia is determined from a liquid m-TDA sample such as can be obtained from the feed stream of the evaporator or by complete condensation of a part stream of the gas stream leaving the evaporator. The sample is purged with a stream of nitrogen in a high-grade steel autoclave at 140° C. for 1 h and the physically dissolved ammonia is discharged from the m-TDA in this way. The stream of nitrogen is freed from entrained TDA outside the autoclave and the ammonia is neutralized in an excess of dilute sulfuric acid in a gas wash bottle. The consumption of sulfuric acid and therefore the amount of physically dissolved ammonia is determined by back-titration of the sulfuric acid content with 0.1 N sodium hydroxide solution.

Example 1 (Comparative)

Use of m-TDA which has been Topped up with Nickel Salts

To demonstrate the influence of heavy metal ions on the release of ammonia, 603 g of an m-TDA from which the residue had not been removed and to which 0.12 g of nickel in the form of a nickel(II) salt were added, so that a nickel ion concentration of 200 ppm resulted, were employed in Example 1. This m-TDA had a residue content of 1.13 wt. %, while the content of cycloaliphatic amines was 0.12 wt. % and the content of physically dissolved ammonia was 25 ppm. This m-TDA to which nickel ions had been added was exposed to a temperature of 320° C. for 5 h, and in this period of time showed an extremely high release of ammonia of 8,155 mg/kg of m-TDA.

Example 2 (Comparative)

Residue Formation During Heat Treatment of m-TDA which was Pure in the Technical Sense 599 g of m-TDA which had been distilled beforehand and in this way freed from heavy metals, TDA residue and cycloaliphatic amines were employed in Example 2. In the technical sense, the sample was free from heavy metals (<10 ppm) and residue-free (<0.05 wt. % of TDA residue) and it was possible to reduce the content of cycloaliphatic amines to 0.02 wt. %. The content of physically dissolved ammonia was 31 ppm. This sample was exposed to a temperature of 320° C. for 5 h, and in this period of time showed a release of ammonia, which exceeded the release of the physically dissolved ammonia, of 89 mg/kg of m-TDA. After the heat treatment, the residue content was determined again. An increase to 1.01 wt. % was determined.

Example 3 (Comparative)

A stream comprising 3,140 kg/h of a mixture containing 1.2 wt. % of TDA residue, 50 ppm of $NH_3$, 500 ppm of cycloaliphatic amines and 3 ppm of heavy metals, the remainder essentially being m-TDA, was fed to an evaporator in which 2,400 kg/h of the mixture vaporized and were fed to a gas phase phosgenation. 739 kg/h (i.e., 23.5 wt. %) of the intake stream were sluiced out and fed to another use. The evaporator was designed as a falling film evaporator with a pump reservoir and circulating pump and was operated at 320° C. under 1.2 bar. The pump reservoir corresponded to the bottom of the evaporator. The working volume in the pump reservoir was 1.2 $m^3$, which corresponded to an amount of liquid held in the evaporator of approx. 1,020 kg. The ratio of the amount of liquid held in the bottom of the evaporator to the stream vaporized was 0.4 h. The ammonia content in the stream to the gas phase phosgenation was approx. 90 ppm, and rapid blocking was observed.

Example 4 (Comparative)

A stream composed of 2,402 kg/h of a mixture which was free from residue and heavy metals in the technical sense and contained 1,000 ppm of cycloaliphatic amines and 12 ppm of ammonia, the remainder essentially being m-TDA, was fed to the arrangement from Example 3. Approx. 2,400 kg/h were vaporized, and approx. 2 kg/h (i.e., 0.08 wt. % of the intake stream) were sluiced out and fed to another use. The working volume in the pump reservoir was 1.2 $m^3$, which corresponded to an amount of liquid held in the evaporator of approx. 1,020 kg. The ratio of the amount of liquid held in the bottom of the evaporator to the stream vaporized was 0.4 h. The ammonia content in the stream to the gas phase phosgenation was approx. 76 ppm, and noticeable blocking was observed.

Example 5 (Comparative)

A stream composed of 2,450 kg/h of a mixture which was free from residue and heavy metals in the technical sense and contained 1,000 ppm of cycloaliphatic amines and 12 ppm of ammonia, the remainder essentially being m-TDA, was fed to the arrangement from Example 3. Approx. 2,400 kg/h were vaporized, and approx. 50 kg/h (i.e., 2.0 wt. % of the intake stream) were sluiced out and fed to another use. The working volume in the pump reservoir was 6 $m^3$, which corresponded to an amount of liquid held in the evaporator of approx. 5,100 kg. The ratio of the amount of liquid held in the bottom of the evaporator to the stream vaporized was 2.1 h. The ammonia content in the stream to the gas phase phosgenation was approx. 137 ppm, and rapid blocking was observed.

Example 6

A stream composed of 2,424 kg/h of a mixture which was free from heavy metals in the technical sense and contained 200 ppm of cycloaliphatic amines, 14 ppm of ammonia and 0.1 wt. % of residue, the remainder essentially being m-TDA, was fed to the arrangement from Example 3. Approx. 2,400 kg/h were vaporized, and approx. 24 kg/h (i.e., 1.0 wt. % of the intake stream) were sluiced out and fed to another use. The working volume in the pump reservoir was 1.2 m³. The ratio of the amount of liquid held in the bottom of the evaporator to the stream vaporized was 0.4 h. The ammonia content in the stream to the gas phase phosgenation was approx. 30 ppm, and a lower tendency towards blocking compared with Examples 3 to 5 and an increased number of operating hours were observed.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of m-toluene-diisocyanate comprising:
   (1) generating a gaseous stream of meta-toluenediamine by vaporizing liquid meta-toluenediamine comprising an isomer mixture of 2,4-meta-toluenediamine and 2,6-meta-toluenediamine in at least one evaporator, by:
      (a) feeding to the evaporator liquid meta-toluenediamine containing:
         (i) less than 0.5 wt. %, based on weight of meta-toluenediamine, of toluenediamine residue, and in total less than 0.2 wt. %, based on weight of meta-toluenediamine, of ammonia and cycloaliphatic amines, and
         (ii) less than 20 ppm, based on weight of meta-toluenediamine, of heavy metals, and
      (b) conducting the vaporization under conditions such that a ratio of amount of liquid meta-toluenediamine V in kg present in the evaporator to amount of gas stream M in kg/h leaving the evaporator is less than 2 h, and
      (c) partly vaporizing the liquid meta-toluenediamine in the evaporator to an extent such that at least 0.1 wt. %, based on weight of meta-toluenediamine, of the liquid meta-toluenediamine is not vaporized, and
   (2) feeding to a reactor a gaseous stream of phosgene and the gaseous stream of meta-toluenediamine produced in step (1) to thereby phosgenate the meta-toluenediamine in the gas phase to form m-toluene diisocyanate, provided that the non-vaporized meta-toluenediamine is not included with the gaseous stream fed to the reactor.

2. The process of claim 1 in which the meta-toluenediamine fed to at least one evaporator contains
   a1) less than 50 ppm, based on weight of the meta-toluenediamine, of ammonia and
   a2) less than 0.1 wt. %, based on weight of the meta-toluenediamine, of cycloaliphatic amines.

3. The process of claim 1 in which in step d) the non-vaporized content of meta-toluenediamine is sluiced out of the evaporator through an exit opening and is then partly fed to the evaporator again through an intake opening.

4. The process of claim 1 in which in step d) the non-vaporized content of meta-toluenediamine is sluiced out of the evaporator through an exit opening and is then at least partly fed into the distillation of crude toluenediamine obtained from the hydrogenation of dinitrotoluene.

5. The process of claim 1, wherein the isomer mixture comprises from 78 to 82 wt % of 2,4-toluenediamine and 18 to 22 wt. % 2,6-toluenediamine.

6. The process of claim 1, wherein the process is conducted on an industrial scale.

7. A process for the preparation of m-toluene-diisocyanate comprising:
   (1) generating a gaseous stream of meta-toluenediamine by vaporizing liquid meta-toluenediamine comprising an isomer mixture of 2,4-meta-toluenediamine and 2,6-meta-toluenediamine in at least one evaporator, by:
      (a) heat treating liquid meta-toluenediamine at not less than 100° C. for at least 15 minutes so that the ammonia formed thereby is removed; and
      (b) feeding to the evaporator the heat treated liquid meta-toluenediamine wherein the meta-toluenediamine contains:
         (i) in total less than 0.2 wt. %, based on weight of meta-toluenediamine, of ammonia and cycloaliphatic amines, and
         (ii) less than 20 ppm, based on weight of meta-toluenediamine, of heavy metals, and
      (c) conducting the vaporization under conditions such that a ratio of amount of liquid meta-toluenediamine V in kg present in the evaporator to amount of gas stream M in kg/h leaving the evaporator is less than 2 h, and
      (d) partly vaporizing the liquid meta-toluenediamine in the evaporator to an extent such that at least 0.1 wt. %, based on weight of meta-toluenediamine, of the liquid meta-toluenediamine is not vaporized, and
   (2) feeding to a reactor a gaseous stream of phosgene and the gaseous stream of meta-toluenediamine produced in step (1) to thereby phosgenate the meta-toluenediamine in the gas phase to form m-toluene diisocyanate, provided that the non-vaporized meta-toluenediamine is not included with the gaseous stream fed to the reactor.

8. The process of claim 1, wherein the isomer mixture comprises from 78 to 82 wt. % of 2,4-toluenediamine and 18 to 22 wt. % 2,6-toluenediamine.

9. The process of claim 7, wherein the process is conducted on an industrial scale.

* * * * *